United States Patent
Sone et al.

(10) Patent No.: US 9,808,141 B2
(45) Date of Patent: Nov. 7, 2017

(54) ENDOSCOPE

(71) Applicant: OLYMPUS CORPORATION, Tokyo (JP)

(72) Inventors: Nobuhiko Sone, Tokyo (JP); Hideyasu Takato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/724,177

(22) Filed: May 28, 2015

(65) Prior Publication Data

US 2015/0257630 A1    Sep. 17, 2015

Related U.S. Application Data

(63) Continuation of application No. PCT/JP2014/063513, filed on May 21, 2014.

(30) Foreign Application Priority Data

May 22, 2013 (JP) ................................. 2013-108141

(51) Int. Cl.
*G02B 23/24* (2006.01)
*G02B 23/26* (2006.01)
(Continued)

(52) U.S. Cl.
CPC ............ *A61B 1/00096* (2013.01); *A61B 1/00* (2013.01); *A61B 1/05* (2013.01); *A61B 1/0676* (2013.01);
(Continued)

(58) Field of Classification Search
CPC ....... A61B 1/0676; A61B 1/00096; A61B 1/05; A61B 1/00096; A61B 1/06; A61B 1/0607;
(Continued)

(56) References Cited

U.S. PATENT DOCUMENTS 4,272,156 A    6/1981  Ishibashi et al.
4,415,240 A *  11/1983  Nishioka ............ A61B 1/00096
                                                    385/117
(Continued)

FOREIGN PATENT DOCUMENTS

GB          2011111 A     7/1979
JP          02-302713    12/1990
(Continued)

OTHER PUBLICATIONS

International Search Report, dated Aug. 26, 2014, issued in corresponding International Application No. PCT/JP2014/063513.
(Continued)

*Primary Examiner* — Timothy J Neal
*Assistant Examiner* — Aaron B Fairchild
(74) *Attorney, Agent, or Firm* — Andrews Kurth Kenyon LLP

(57) ABSTRACT

An endoscope includes an observation optical system that allows a magnified observation close to a subject, and illumination optical systems. In a close observation, $I_{TM}$ is a maximum brightness within an observation view field angle, and $I_{TC}$ is a center brightness. In a normal observation $I_{WC}$ is a center brightness, and $I_{WS}$ is a brightness at a position of 80% of a maximum view angle. The following is satisfied:

$0.3 < I_{TC}/I_{TM} < 0.45$ $0.15 < I_{WS}/I_{WC} < 0.25$ $0.3 < f_L f_T / \phi_L I_H < 0.6$ where $f_L$ is a focal length of each of the entire illumination optical systems, $f_T$ is a focal length of the entire observation optical system in a maximum magnification, $\phi_L$ is an outer diameter of a lens that is farthest on an object side of each
(Continued)

illumination optical system, and $I_H$ is a maximum image height of the observation optical system.

9 Claims, 9 Drawing Sheets

(51) Int. Cl.
*A61B 1/06* (2006.01)
*A61B 1/00* (2006.01)
*A61B 1/05* (2006.01)

(52) U.S. Cl.
CPC ....... *G02B 23/243* (2013.01); *G02B 23/2423* (2013.01); *G02B 23/26* (2013.01)

(58) Field of Classification Search
CPC ..... A61B 1/0615; A61B 1/0623; A61B 1/063; A61B 1/0638; A61B 1/0646; A61B 1/0653; A61B 1/0661; A61B 1/0669; A61B 1/0684; G02B 23/243; G02B 23/2423; G02B 23/26
USPC ......................................................... 600/177
See application file for complete search history.

(56) References Cited

U.S. PATENT DOCUMENTS

| | | | | |
|---|---|---|---|---|
| 4,721,372 A * | 1/1988 | Yokota | ................. | G02B 23/243 359/658 |
| 4,736,734 A * | 4/1988 | Matsuura | ................. | G02B 7/10 348/68 |
| 4,874,232 A * | 10/1989 | Hasegawa | ............ | G02B 23/243 359/690 |
| 5,861,987 A * | 1/1999 | Nakamura | ......... | G02B 23/2415 359/429 |
| 5,980,454 A * | 11/1999 | Broome | ................... | A61B 1/05 359/565 |
| 6,036,343 A * | 3/2000 | Tomioka | ................... | A61B 1/07 362/268 |
| 6,252,723 B1 * | 6/2001 | Nagaoka | ............... | G02B 15/173 359/652 |
| 7,215,478 B1 * | 5/2007 | Hirata | ..................... | G02B 21/33 359/656 |
| 2001/0031912 A1 * | 10/2001 | Adler | .................. | A61B 1/00096 600/109 |
| 2005/0054901 A1 * | 3/2005 | Yoshino | ............. | A61B 1/00096 600/176 |
| 2006/0052668 A1 * | 3/2006 | Homma | .................... | A61B 1/07 600/177 |
| 2009/0161234 A1 * | 6/2009 | Sasamoto | .......... | G02B 23/2407 359/717 |
| 2010/0080016 A1 * | 4/2010 | Fukui | ................... | A61B 1/0653 362/574 |
| 2012/0147165 A1 | 6/2012 | Yoshino et al. | | |
| 2013/0310649 A1 * | 11/2013 | Sone | .................. | A61B 1/00096 600/177 |
| 2014/0233110 A1 * | 8/2014 | Sone | ........................ | G02B 9/14 359/738 |

FOREIGN PATENT DOCUMENTS

| | | |
|---|---|---|
| JP | 10-239740 | 9/1998 |
| JP | 11-311744 | 11/1999 |
| JP | 2000-037345 | 2/2000 |
| JP | 2001-346752 | 12/2001 |
| JP | 2003-037345 | 2/2003 |
| JP | 2003-102679 | 4/2003 |
| JP | 2003-235789 | 8/2003 |
| JP | 2012-135432 | 7/2012 |

OTHER PUBLICATIONS

Extended European Search Report, dated Dec. 22, 2016, from corresponding European Application No. 14800911.1.

* cited by examiner

ENDOSCOPE

CROSS-REFERENCE TO RELATED APPLICATIONS

This application is a Continuation Application of International Application PCT/JP2014/063513 filed on May 21, 2014, which claims priority to Japanese Application No. 2013-108141 filed on May 22, 2013.

The Contents of International Application PCT/JP2014/063513 and Japanese application No. 2013-108141 are hereby incorporated by reference herein in its entirety.

TECHNICAL FIELD

The present invention relates to an endoscope including illumination optical systems and an observation optical system.

BACKGROUND ART

Typically, in a distal end portion of an endoscope, structural objects such as an illumination optical system for illuminating a subject, an observation optical system including, at a distal end face thereof, an optical member for receiving incoming light from the subject, a channel that guides a treatment instrument, and a nozzle for cleaning dirt adhering to a lens surface of the image pickup optical system are provided.

An endoscope including an observation optical system that allows magnified close observation allows not only normal observation but also close observation by moving a part of lenses in the observation optical system and thereby changing a focal length. However, since a same illumination optical system is used for both normal observation and close observation, in particular, in a close observation in which a distance to a subject is no more than 2 mm, a peripheral part of a screen is brighter than a center of the same because of the layout of the illumination optical system. Therefore, when a subject to be focused on is positioned at the center part, a favorable observation cannot be performed because of insufficient distribution of illuminating light.

PTL 1 discloses an endoscope that provides only small illumination unevenness in a magnified close observation and thus enables illumination of a subject with sufficient brightness by setting a variable range of a best focal position within a range in which illuminating light beams emitted from a plurality of illumination windows overlap.

Also, PTL 2 discloses an endoscope that minimizes unevenness in an observation area in close observation by providing illumination means at respective positions on opposite sides of an observation optical system at which an illuminance of a peripheral part of the observation area is no more than twice an illuminance of a center part of the observation area.

CITATION LIST

Patent Literature

{PTL 1} Japanese Unexamined Patent Application, Publication No. 2001-346752
{PTL 2} Japanese Unexamined Patent Application, Publication No. 2000-37345

SUMMARY OF INVENTION

Technical Problem

However, none of the aforementioned patent literatures takes light distribution in normal observation into consideration, and also has the following problems in close observation.

In other words, the endoscope disclosed in PTL 1 requires a best focal position to be set at a distance that provides sufficiently wide distribution of light from the illumination optical systems, making it difficult to bring the endoscope close to a subject, and thus, is not suitable for magnified observation.

The endoscope disclosed in PTL 2 ensures light distribution by providing a large distance between the observation optical system and the illumination optical systems, resulting in an increase in diameter of a distal end of the endoscope.

The present invention has been made in view of the aforementioned circumstances, and an object of the present invention is to provide an endoscope that ensures sufficient light distribution in both of normal observation and close observation, enabling favorable observation.

Solution to Problem

In order to achieve the above object, the present invention provides the following solutions.

An aspect of the present invention provides an endoscope including: an observation optical system including a plurality of lenses and having a function that allows a magnified observation close to a subject; and a plurality of illumination optical systems each including a plurality of lenses and illuminating the subject with illuminating light, wherein in a close observation in which a distance between a distal end face of the insertion portion and the subject is an arbitrary distance of from 1.5 mm to 2.5 mm, where $I_{TM}$ is a maximum brightness within an observation view field angle and $I_{TC}$ is a center brightness, and in a normal observation in which the distance between the distal end face of the insertion portion and the subject is 50 mm, where $I_{WC}$ is a center brightness and $I_{WS}$ is a brightness at a position of 80% of a maximum view angle, the following conditional expressions are satisfied:

$$0.3 < I_{TC}/I_{TM} < 0.45 \quad (1);$$

$$0.15 < I_{WS}/I_{WC} < 0.25 \quad (2); \text{ and}$$

$$0.3 < f_L f_T / \phi_L I_H < 0.6 \quad (3),$$

where $f_L$ is a focal length of each of the entire illumination optical systems, $f_T$ is a focal length of the entire observation optical system in a maximum magnification, $\phi_L$ is an outer diameter of a lens that is farthest on an object side of each illumination optical system, and $I_H$ is a maximum image height of the observation optical system.

DESCRIPTION OF EMBODIMENTS

An endoscope according to an embodiment of the present invention will be described with reference to the drawings.

Figure 1:
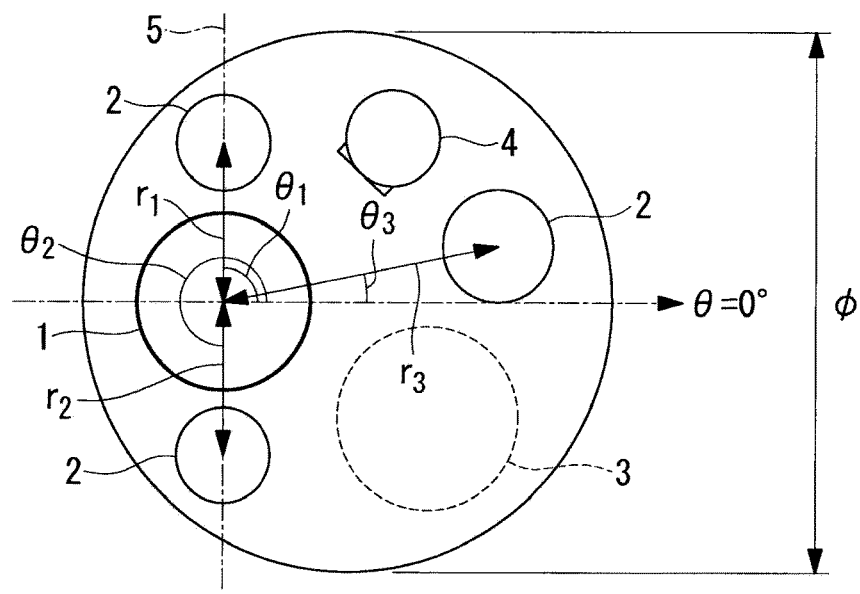
FIG. 1 is a schematic configuration diagram illustrating a front face of a distal end of an insertion portion of an endoscope according to an embodiment of the present invention.

FIG. 1 illustrates a front face of a distal end portion of an insertion portion of an endoscope, and as illustrated in FIG. 1, in the insertion portion, an observation optical system 1 that picks up an image of an observation target, a plurality of illumination optical systems 2 that each distribute illuminating light emitted from a non-illustrated light source and supplied via a light guide fiber, a channel 3 that guides a treatment instrument such as a forceps or a probe, and a nozzle 4 that supplies a fluid or air for cleaning to the observation optical system 1 and the illumination optical systems 2.

In FIG. 1, each of $r_1$ to $r_3$ is a distance between a center of the observation optical system 1 and a center of the relevant illumination optical system 2. As illustrated in FIG. 1, for an azimuth θ, it is assumed that a direction passing through the center of the observation optical system 1, which is a rightward direction in the sheet, is θ=0°, and a counterclockwise direction is a positive direction. For reference, in the example illustrated in FIG. 1, $\theta_1$=90°, $\theta_2$=270° and $\theta_3$=10°.

Figure 2:
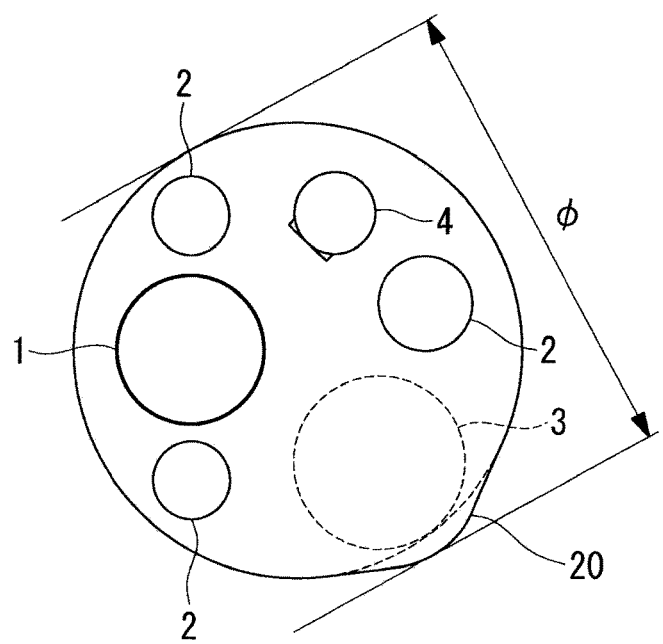
FIG. 2 is a schematic configuration diagram illustrating another example of a front face of a distal end of an insertion portion of an endoscope according to an embodiment of the present invention.

Also, an insertion diameter ϕ of a distal end of the endoscope is a diameter of the distal end portion of the endoscope. However, a structure of the distal end portion of the endoscope may include a projecting odd-shape part 20 provided because of a physical structural object in the insertion portion, for example, where a channel cannot be fully accommodated in a round distal end portion. In such case, as illustrated in FIG. 2, a maximum diameter portion is determined as ϕ.

The observation optical system 1 includes a plurality of lenses and has a function that allows a magnified observation close to a subject. In a magnified close observation state, a distance between the observation optical system 1 and the subject is smaller than a distance between the observation optical system 1 and each of the illumination optical systems 2, and thus, a brightness of a peripheral part is larger than that of a center part. In particular, in magnified close observation, a lesion to be focused on is usually positioned in the center part, favorable observation is hindered unless a ratio of the brightness of the center part relative to that of the peripheral part is high.

Thus, the endoscope is configured so that in a close observation in which a distance between a distal end face of the insertion portion and the subject is an arbitrary distance of from 1.5 mm to 2.5 mm, where $I_{TM}$ is a maximum brightness within an observation view field angle and $I_{TC}$ is a center brightness, the following conditional expression is satisfied:

$$0.3 < I_{TC}/I_{TM} < 0.45 \quad (1).$$

If a value that is below the lower limit of conditional expression (1) is provided, the center part is dark, making it impossible to perform favorable observation when the endoscope is bought close to the subject. On the other hand, if a value exceeding the upper limit is provided, it is possible to perform favorable close observation; however, a distribution of light by each illumination optical system is wide, resulting in deterioration in capability of observation in a depth direction in normal observation.

Here, it is desirable that conditional expression (1) be satisfied with an arbitrary distance between 1.5 mm and 2.5 mm in depth in magnified close observation, and it is more desirable that conditional expression (1) be satisfied with a distance of no more than 2 mm because more favorable observation can be performed as a synergistic effect in combination with a magnified observation (in which a subject can more closely be observed with magnification).

In a normal observation state, there is a sufficient distance to a subject, and thus, a brightness of a center part is larger than that of a peripheral part. Also, in this state, a subject having a depth is observed, and an excessive increase in brightness of the peripheral part hinders favorable observation in the depth direction. On the other hand, an excessive decrease in brightness of the peripheral part hinders favorable observation of the peripheral part, and thus, it is necessary to balance the brightness for observation in the depth direction and the brightness for observation of the peripheral part. Therefore, the endoscope is configured so that in a normal observation in which the distance between the distal end face of the insertion portion and the subject is 50 mm, where $I_{WC}$ is a center brightness and $I_{WS}$ is a brightness at a position of 80% of a maximum view angle, the following conditional expression is satisfied:

$$0.15 < I_{WS}/I_{WC} < 0.25. \quad (2).$$

If a value that is below the lower limit of conditional expression (2) is provided, the peripheral part is excessively dark in a normal observation and sufficient light distribution cannot be ensured in a close observation. On the other hand, if a value exceeding the upper limit of conditional expression (2) is provided, light distribution in a direction toward a center is insufficient, resulting in insufficiency in brightness in the depth direction in a normal observation, and thus hindering favorable observation.

In order to satisfy both conditional expressions (1) and (2), it is necessary to set a focal length of each illumination optical system so as to conform to a focal length of the observation optical system, and thus, it is necessary to satisfy the following conditional expression;

$$0.3 < f_L f_T / \phi_L I_H < 0.6 \qquad (3),$$

where $f_L$ is the focal length of each of the entire illumination optical systems, $f_T$ is the focal length of the entire observation optical system in a maximum magnification, $\phi_L$ is an outer diameter of a lens that is farthest on the object side of the relevant illumination optical system, and $I_H$ is a maximum image height of the observation optical system.

According to the conditional expression, the focal length of the observation optical system and the focal length of each illumination optical system are determined, enabling provision of a well-balanced light distribution capability for both of distant observation and close observation.

If a value that is below the lower limit of conditional expression (3) is provided, the distribution of light by each illumination optical system is excessively wide, hindering observation in the depth direction in a normal observation or a view field range of the observation optical system is wide, resulting in a failure to provide a desired magnifying power in a close observation.

If a value exceeding the upper limit of conditional expression (3) is provided, the distribution of light by the illumination optical system is narrow, resulting in insufficiency in center brightness in a close observation and thus hindering the observation, or the view field range of the observation optical system is narrow, which may result in an oversight of a lesion part.

It is more preferable to employ conditional expression (3)′ below instead of conditional expression (3):

$$0.35 < f_L f_T / \phi_L I_H < 0.55 \qquad (3)'.$$

It is even more preferable to employ conditional expression (3)″ instead of conditional expression (3) or (3)′:

$$0.38 < f_L f_T / \phi_L I_H < 0.52 \qquad (3)''.$$

In order to set a proper light distribution capability of the illumination optical systems, a distance between the observation optical system and each illumination optical system is important. In particular, in close observation, for example, if a distance to a subject is 2 mm, a distance between the observation optical system and the subject is smaller than a distance between the observation optical system and each illumination optical system, which may result in failure of entry of sufficient light. Therefore, it is necessary to satisfy conditional expressions (4) and (5) below:

$$8 < r_1^2 / f_L f_T < 16 \qquad (4); \text{ and}$$

$$8 < r_2^2 / f_L f_T < 16 \qquad (5),$$

where each of $r_1$ and $r_2$ is a distance between a lens disposed farthest on the object side of the observation optical system, and a center of a lens disposed farthest on the object side of the relevant illumination optical system.

If values that are below the respective lower limits of the expressions are provided, the distance between the observation optical system and each of the illumination optical systems is small and thus the observation optical system and each of the illumination optical systems may interfere with each other. If values exceeding the respective upper limits are provided, each of the illumination optical systems is distant from the observation optical system, resulting in failure to maintain a sufficient light distribution capability in close observation, or the focal length of each illumination optical system is small and thus the distribution of light by the illumination optical system is wide, hindering observation in a depth direction in normal observation.

It is more preferable to employ conditional expressions (4)′ and (5)′ below instead of conditional expressions (4) and (5):

$$10 < r_1^2 / f_L f_T < 14 \qquad (4)'; \text{ and}$$

$$10 < r_2^2 / f_L f_T < 14 \qquad (5)'.$$

Examples of factors that affect a close observation include a view field range. As the view field range is narrower, the light distribution becomes more even, enabling favorable observation. On the other hand, as the view field range is wider, the light distribution becomes wider, which may cause a difference in brightness between a bright part and a dark part on an observation screen. Thus, the endoscope is preferably configured so as to satisfy conditional expression (6) below:

$$0.8 < f_T F_{FT} / f_W F_{FW} < 1.1 \qquad (6),$$

where $f_W$ is a focal length of the entire system in a normal observation, $F_{FT}$ is a front-side focal position in a magnified close observation state, and $F_{FW}$ is a front-side focal position in a normal observation state.

If a value that is below the lower limit of conditional expression (6) is provided, wider observation can be performed in close observation, but the center part becomes dark, resulting in failure to perform favorable observation. On the other hand, if a value exceeding the upper limit of conditional expression (6) is provided, as opposed to the above, brightness of the center part can be ensured, but the observation range is limited, resulting in failure to perform wide-range observation.

It is more preferable to employ conditional expression (6)′ below instead of conditional expression (6):

$$0.85 < f_T F_{FT} / f_W F_{FW} < 1.05 \qquad (6)'.$$

It is even more preferable to employ conditional expression (6)″ instead of conditional expression (6) or (6)′:

$$0.9 < f_T F_{FT} / f_W F_{FW} < 1.1 \qquad (6)''.$$

In an observation optical system having a magnified observation function, for favorable observation of a subject, it is desirable to provide a sufficient magnification factor in maximum magnification.

Thus, the endoscope is preferably configured so as to satisfy conditional expression (7) below:

$$0.3 < |1 \times \beta / I_H| < 0.45 \qquad (7),$$

where $\beta$ is a paraxial magnifying power in a maximum magnification in the observation optical system.

Conditional expression (7) indicates a magnification factor of a case where a subject having a size of 1 mm passes through the observation optical system, and if a value that is below the lower limit of conditional expression (7) is provided, a sufficient magnifying power cannot be ensured, resulting in failure to perform favorable observation. On the other hand, if a value exceeding the upper limit of conditional expression (7) is provided, a sufficient magnifying power can be ensured, but the optical system becomes a narrow-angle one with a limited observation range, resulting in failure to perform favorable observation.

Also, in an observation optical system having a magnified observation function, in order to perform favorable observation, an image pickup device desirably has a large number of pixels. Thus, the endoscope is preferably considered so as to satisfy conditional expression (8) below:

$$0.25 < I_H/(1000P) < 0.5 \tag{8},$$

where P is a pixel pitch of an image pickup device included in the observation optical system.

If a value that is below the lower limit of conditional expression (8) is provided, a pixel pitch is large, or an image pickup device is small, and thus, no image pickup device with a large number of pixels is provided. If a value exceeding conditional expression (8) is provided, a large number of pixels is provided, but the pixel pitch is small, and thus, the effect of diffraction is strong, and therefore, if a sufficient magnifying power is provided, the problem of blurring easily occurring, which results in difficulty in focusing, occurs.

If each illumination optical system includes three convex lenses, a ratio between a focal length of a lens that is farthest on the object side face from among the three convex lenses and a focal length of the entire system has a large impact. Thus, it is preferable to satisfy conditional expression (9) below:

$$1.4 < f_{L1}/f_L < 3.2 \tag{9},$$

where $f_{L1}$ is a focal length of a lens that is farthest on the object side of each illumination optical system.

If a value that is below the lower limit of conditional expression (9) is provided, the light distribution is wide, and thus, favorable observation can be performed in close observation; however, observation in the depth direction is difficult in normal observation. On the other hand, if a value exceeding conditional expression (9) is provided, the light distribution is narrow, and thus, the brightness of a part around a center is insufficient in close observation.

It is more preferable to employ conditional expression (9)' below instead of conditional expression (9):

$$1.6 < f_{L1}/f_L < 2.4 \tag{9}'.$$

It is even more preferable to employ conditional expression (9)'' instead of conditional expression (9) or (9)':

$$1.7 < f_{L1}/f_L < 2.2 \tag{9}''.$$

For balancing close observation and normal observation, in particular, for favorable normal observation, it is necessary to suppress an amount of variation in an angular direction in a light distribution capability of each illumination optical system. A large amount of variation increases the brightness of the part around the center, and on the other hand, a small amount of variation increases the brightness of a part around a periphery. Thus, the endoscope is preferably configured so that in at least two illumination optical systems of the plurality of illumination optical systems, where a brightness in a direction toward a center at a distance of 50 mm is 1, a brightness $\gamma$ ($\alpha$) of an arbitrary angle $\alpha$ (°) satisfies conditional expression (10) below:

$$0.21 < \gamma(50)/\gamma(25) < 0.39 \tag{10}.$$

If a value that is below the lower limit of conditional expression (10) is provided, in normal observation, the brightness of the part around the center is increased, allowing favorable observation in a depth direction, but no sufficient light is provided to the peripheral part, resulting in deterioration in observation capability. On the other hand, if a value exceeding the upper limit of conditional expression (10) is provided, the brightness of the peripheral part is increased, allowing favorable observation, but the observation capability in the depth direction deteriorates.

It is more preferable to employ conditional expression (10)' below instead of conditional expression (10):

$$0.23 < \gamma(50)/\gamma(25) < 0.34 \tag{10}'.$$

In close observation, in particular, the layout of an observation optical system and illumination optical systems has a large impact. If an observation optical system is positioned far from one of two illuminations arranged symmetrically, the side on which the far illumination is dark and brightness concentrates only on one direction on an observation screen, which makes the observation screen appear to have uneven light distribution. Thus, the endoscope is preferably configured so that at least two illumination optical systems of the plurality of illumination optical systems satisfy the following conditional expression:

$$0.8 < r_1/r_2 < 1.2 \tag{11}.$$

If a value that falls outside of the range determined by conditional expression (11) is provided, for example, the problem of uneven light distribution such as only the left side being bright and thus causing deterioration in capability of observation of the right side occurs.

It is more preferable to employ conditional expression (11)' below instead of conditional expression (11):

$$0.9 < r_1/r_2 < 1.1 \tag{11}'.$$

It is even more preferable to employ conditional expression (11)'' instead of conditional expression (11) or (11)':

$$0.94 < r_1/r_2 < 1.06 \tag{11}''.$$

In the layout, the angular direction also affects the unevenness, and thus, illumination optical systems are favorably installed in directions symmetrical to each other with reference to the image pickup optical system, and a degree of the symmetry is favorably higher. Thus, the endoscope is preferably configured so as to satisfy conditional expression (12) below:

$$165 < |\theta_1 - \theta_2| \leq 180 \tag{12},$$

where each of $\theta_1$ and $\theta_2$ is an azimuth relative to the direction toward the center.

If a value exceeding a range determined by conditional expression (12) is provided, the problem of light distribution unevenness such as a plurality of parts that are unevenly bright being generated, for example, such as only upper right and upper left parts being illuminated and thus deterioration in capability of observation of the lower side.

It is more preferable to employ conditional expression (12)' below instead of conditional expression (12):

$$170 < |\theta_1 - \theta_2| \leq 180 \tag{12}'.$$

It is even more preferable to employ conditional expression (12)'' instead of conditional expression (12) or (12)':

$$175 < |\theta_1 - \theta_2| \leq 180 \tag{12}''.$$

Furthermore, regarding the layout, typically, a smaller diameter of a distal end of an endoscope is desirable, and thus, the endoscope is preferably configured so that the distance between the image pickup optical system and each of the illumination optical systems and the diameter of the distal end satisfy conditional expression (13) below:

$$0.06 < r_1 r_2 / \phi^2 < 0.15 \qquad (13).$$

If a value that is below the lower limit of conditional expression (13) is provided, the diameter of the distal end is large. On the other hand, if a value exceeding the upper limit of conditional expression (13) is provided, the diameter of the distal end can be made small, but limitations on arrangement of, e.g., the observation optical system and the illumination optical systems become tight, causing the problem of a failure to fully accommodate these optical systems within the diameter of the distal end.

It is more preferable to employ conditional expression (13)' below instead of conditional expression (13):

$$0.07 < r_1 r_2 / \phi^2 < 0.13 \qquad (13)'.$$

It is even more preferable to employ conditional expression (13)" instead of conditional expression (13) or (13)':

$$0.08 < r_1 r_2 / \phi^2 < 0.11 \qquad (13)''.$$

Since an distal end portion of an endoscope includes not only an observation optical system and illumination optical systems, but also structural objects such as a hole, called a channel, for letting a treatment instrument out and a nozzle for cleaning lenses, in particular, where three illumination optical systems are arranged, it may be difficult to arrange all of illumination optical systems symmetrically to one another with reference to an observation optical system. In such case, it is desirable to make distances of the three illumination optical systems from the observation optical system be equal to one another, and the endoscope is preferably configured so as to satisfy conditional expression (14) below:

$$0.8 < \min(r_1, r_2, r_3) / \operatorname{Max}(r_1, r_2, r_3) \le 1.0 \qquad (14),$$

where each of $r_1$, $r_2$ and $r_3$ is a distance of the center of the lens disposed farthest on the object side of the observation optical system and a center of a lens disposed farthest on the object side of the relevant illumination optical system.

As a result of conditional expression (14) being satisfied, the illumination optical systems are equally arranged, enabling suppression of light distribution unevenness and thus illuminating light is illuminated evenly, and thus, the observation capability can be enhanced.

It is more preferable to employ conditional expression (14)' below instead of conditional expression (14):

$$0.9 < \min(r_1, r_2, r_3) / \operatorname{Max}(r_1, r_2, r_3) \le 1.0 \qquad (14)'.$$

Also, it is even more preferable to employ conditional expression (14)" instead of conditional expression (14) or (14)':

$$0.94 < \min(r_1, r_2, r_3) / \operatorname{Max}(r_1, r_2, r_3) \le 1.0 \qquad (14)''.$$

Figure 3:
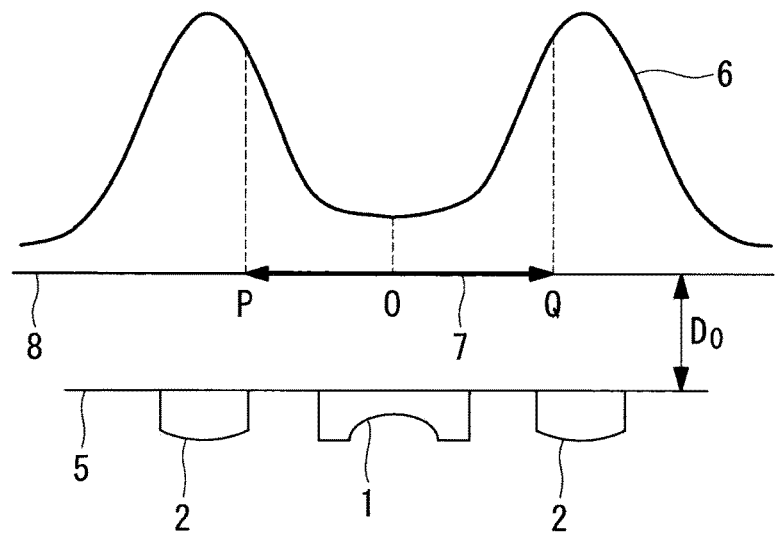
FIG. 3 is a diagram illustrating a relationship between an endoscope according to an embodiment of the present invention and a subject in a close observation.

FIG. 3 illustrates a configuration in a close observation. A subject 8 is located at a position that is a distance $D_0$ from a distal end face 5 of the endoscope that passes through the centers of the observation optical system 1 and the illumination optical systems 2, and 0 is a center of an observation range 7 of the observation optical system 1, each of P and Q is an extreme periphery.

Also, a light distribution characteristic 6 of the illumination optical systems 2 is provided, $I_{TM}$ is a brightness of a part that is brightest between P and Q, and $I_{TC}$ is a brightness at the center O. A characteristic in close observation lies in that since the distance $D_0$ is from 1.5 mm to 2.5 mm and thus small, the light distribution characteristic 6 indicates that the brightness of the peripheral part of the observation range is larger than the brightness of the center part of the observation range.

Although FIGS. 1 and 3 each indicate a case where an observation optical system and illumination optical systems are located on a same straight line, it should be understood that a maximum brightness and a center brightness in an observation range can also be defined as $I_{TM}$ and $I_{TC}$, respectively, in a case other than the above case.

Figure 4:
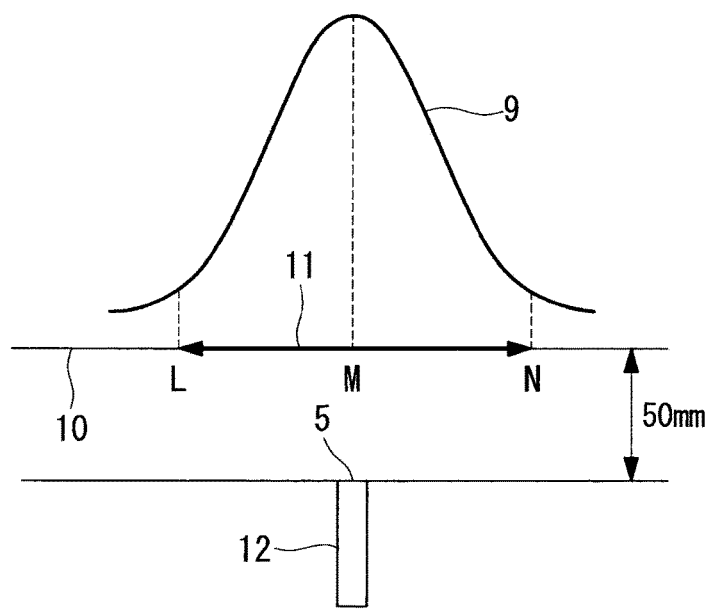
FIG. 4 is a diagram illustrating a relationship between an endoscope according to an embodiment of the present invention and a subject in a normal observation.

Next, FIG. 4 illustrates a configuration in a normal observation. A subject 10 is located at a position that is a distance of 50 mm away from the distal end face 5 of the endoscope, and M is a center of a view field range 11 of the observation optical system, and each of L and N is a position that is 80% of a maximum view angle. Also, a light distribution characteristic 9 of the illumination optical systems is provided, and $I_{WS}$ is a brightness at each of L and N and $I_{WC}$ is a brightness at the center part M. A characteristic of normal observation lies in that when the distance of 50 mm is reached, the light distribution characteristic 9 indicates that the impact of the layout of the illumination optical systems is small and exhibits a shape that is substantially even with reference to the center.

Figure 5:
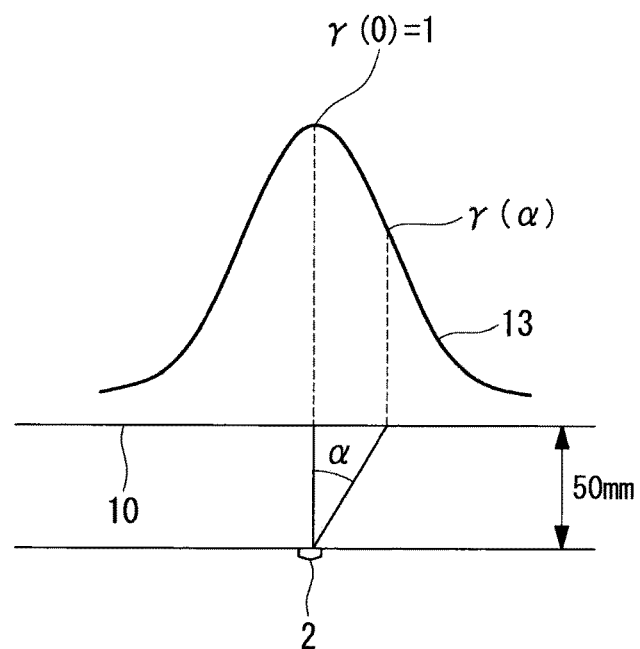
FIG. 5 is a diagram illustrating a light distribution characteristic of an illumination optical system employed in an endoscope according to an embodiment of the present invention.

FIG. 5 illustrates a light distribution characteristic of one illumination optical system.

A light distribution 13 to a subject 10 that is a distance of 50 mm away from an illumination optical system 2 is provided. Here, where the upper side in the sheet of FIG. 5 is 0°, a brightness at a position of 0° is defined as $\gamma(0)=1$, and a brightness at a position that is an angle $\alpha$ away from the position of 0° in a clockwise direction is defined as $\gamma(\alpha)$. Since the light distribution exhibits symmetry, and thus, the position may be a position that is an angle $\alpha$ away from the position of 0° in a counterclockwise direction.

As described above, the present embodiment enables a ratio of a brightness of a center part relative to that of a peripheral part not only in normal observation but also in magnified close observation, ensuring sufficient light distribution and thus allowing favorable observation in both normal observation and close observation.

EXAMPLES

Next, Examples 1 to 3 of the endoscope according to the present embodiment described above will be described with reference to FIGS. 6 to 12. In lens data indicated in each example, r is a curvature radius (unit: mm), d is a surface spacing (mm), Nd is a refractive index for a d line, and Vd is an Abbe number for a d line.

Example 1

Figure 6:
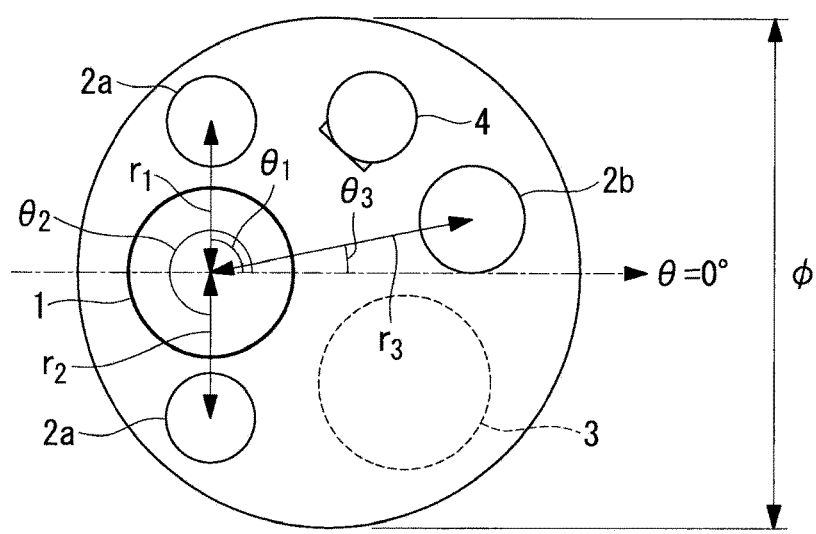
FIG. 6 is a schematic configuration diagram illustrating a front face of a distal end of an insertion portion of an endoscope according to Example 1 of the present invention.

A front view of a distal end of an insertion portion of an endoscope according to Example 1 of the present invention is illustrated in FIG. 6. In Example 1, a total of three illumination optical systems, which are two identical illumination optical systems 2a and an illumination optical system 2b, are employed.

In the present example, $r_1=3.2$, $r_2=3.2$, $r_3=5.16$, $\theta_1=90°$, $\theta_2=270°$, $\theta_3=8.9°$ and $\phi=9.9$.

Figure 7:
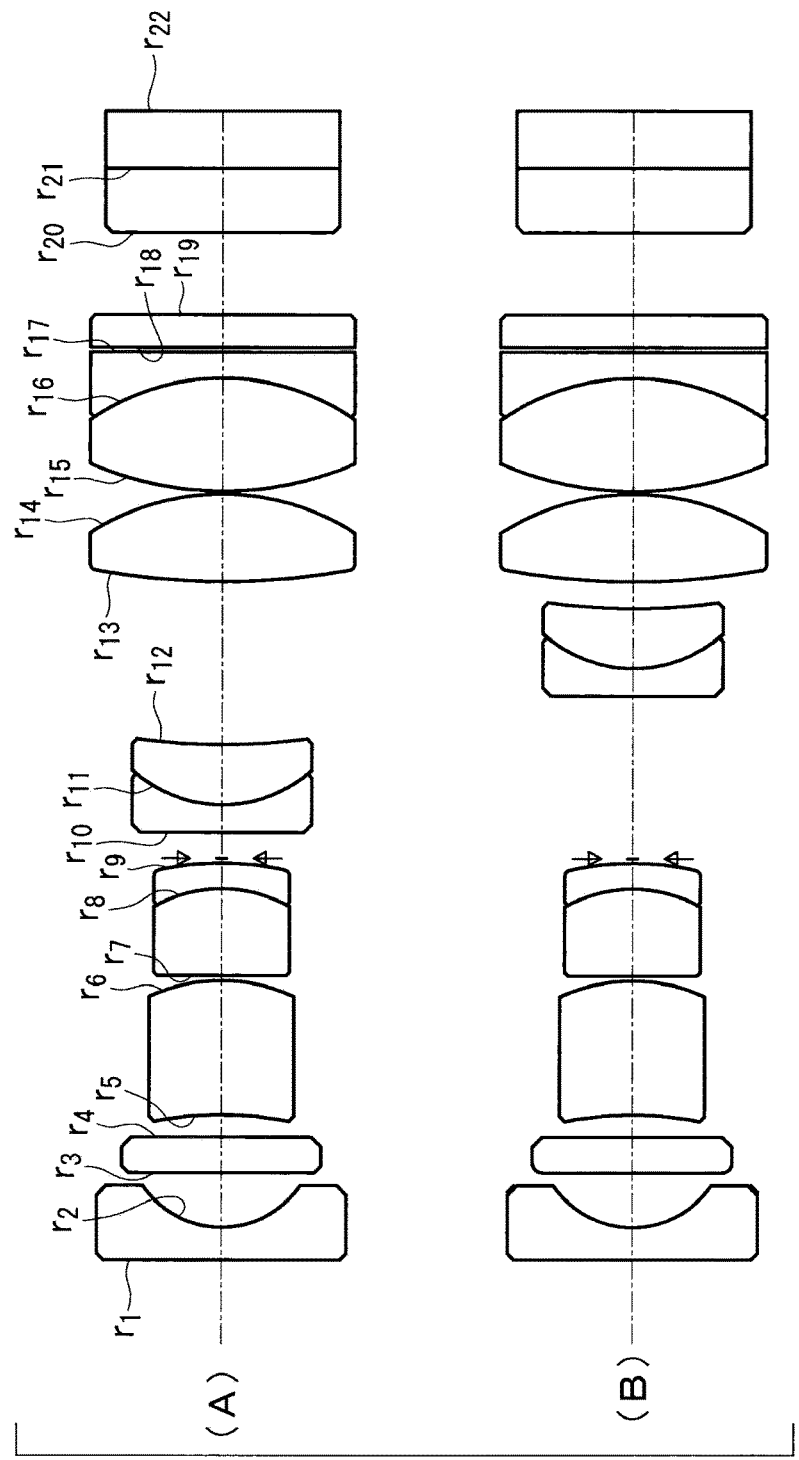
FIG. 7 includes cross-sectional diagrams each illustrating an overall configuration of an observation optical system employed in the endoscope according to Example 1 of the present invention.
Figure 8:
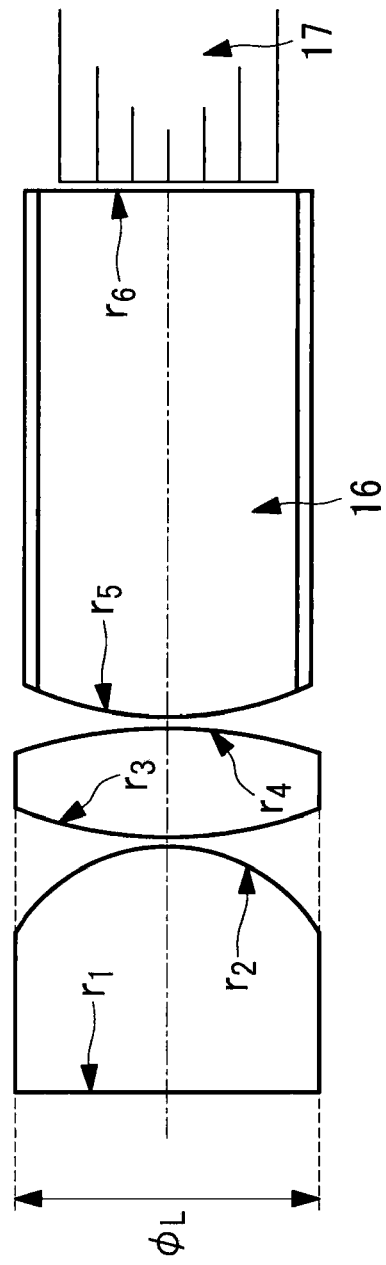
FIG. 8 is a cross-sectional diagram illustrating an overall configuration of an illumination optical system employed in the endoscope according to Example 1 of the present invention.

FIG. 7 illustrates a lens configuration of an observation optical system 1 employed in the endoscope according to the present example, and FIG. 8 illustrates a lens configuration of the illumination optical systems 2a and 2b employed in the endoscope according to the present example.

Lens data of the observation optical system according to Example 1 of the present invention are indicated below.

Lensdata

| Surfacenumber | r | d | Nd | Vd |
|---|---|---|---|---|
| Objectsurface | ∞ | d0 | | |
| 1 | ∞ | 0.40 | 1.883 | 40.76 |
| 2 | 1.11 | 0.63 | | |
| 3 | ∞ | 0.40 | 1.521 | 65.13 |
| 4 | ∞ | 0.30 | | |
| 5 | −4.49 | 1.56 | 1.517 | 52.43 |
| 6 | −2.21 | 0.06 | | |
| 7 | ∞ | 0.97 | 1.750 | 35.33 |
| 8 | −1.56 | 0.36 | 1.923 | 18.9 |
| 9 | −2.70 | 0.03 | | |
| 10(Diaphragm) | ∞ | d10 | | |
| 11 | ∞ | 0.40 | 1.697 | 55.53 |
| 12 | 1.58 | 0.71 | 1.581 | 40.75 |
| 13 | 7.99 | d13 | | |
| 14 | 8.97 | 1.00 | 1.591 | 61.14 |
| 15 | −2.98 | 0.05 | | |
| 16 | 4.00 | 1.30 | 1.488 | 70.23 |
| 17 | −2.68 | 0.30 | 1.923 | 18.9 |
| 18 | ∞ | 0.06 | | |
| 19 | ∞ | 0.36 | 1.523 | 58.5 |
| 20 | ∞ | 0.94 | | |
| 21 | ∞ | 0.84 | 1.516 | 64.14 |
| 22 | ∞ | 0.66 | 1.505 | 63.26 |
| 23(Imageplane) | ∞ | | | |

Variousdata

| | Normalobservation | Maximummagnification |
|---|---|---|
| d0 | 50 | 2 |
| d10 | 0.3 | 1.9 |
| d13 | 1.9 | 0.3 |
| Focallength | 1.24 | 1.40 |
| Front-sidefocalposition | 0.97 | 0.85 |
| Maximumimageheight | 1.2 | 1.2 |
| Paraxialmagnifyingpower | — | −0.49 |
| Pixelpitch | 0.0042 | 0.0042 |

Next, lens data of the illumination optical systems $2a$ according to Example 1 of the present invention are indicated below.

Here, $\phi_L = 1.3$, and a clad of a glass rod 16 was formed by glass having a refractive index of 1.520. In this case, $f_L = 0.54$ and $f_{L1} = 1.14$.

Lensdata

| Surfacenumber | r | d | Nd |
|---|---|---|---|
| 1 | ∞ | 1.11 | 1.883 |
| 2 | −1.01 | 0.04 | |
| 3 | 1.20 | 0.65 | 1.883 |
| 4 | ∞ | 0 | |
| 5 | 1.26 | 2.75 | 1.805 |
| 6 | ∞ | | |

Next, lens data of the illumination optical system $2b$ according to Example 1 of the present invention are indicated below.

Here, $\phi_L = 1.7$, and a clad of a glass rod 16 was formed by glass having a refractive index of 1.520. In this case, $f_L = 0.72$ and $f_{L1} = 2.25$.

Lensdata

| Surfacenumber | r | d | Nd |
|---|---|---|---|
| 1 | ∞ | 1.30 | 1.883 |
| 2 | −2.00 | 0.04 | |
| 3 | 2.00 | 0.75 | 1.883 |
| 4 | −2.00 | 0.05 | |
| 5 | 1.91 | 2.90 | 1.730 |
| 6 | ∞ | | |

Also, a light guide fiber 17 that guides illuminating light from a non-illustrated light source to an illumination optical system has a light distribution characteristic that depends on the angle, and thus, this characteristic is indicated below.

TABLE 1

| ANGLE α | ILLUMINANCE γ (α) |
|---|---|
| 0 | 1.00 |
| 5 | 0.97 |
| 10 | 0.94 |
| 15 | 0.85 |
| 20 | 0.67 |
| 25 | 0.46 |
| 30 | 0.27 |
| 35 | 0.13 |
| 40 | 0.05 |
| 45 | 0.01 |
| 50 | 0.00 |
| 55 | 0.00 |
| 60 | 0.00 |
| 65 | 0.00 |
| 70 | 0.00 |
| 75 | 0.00 |

A light distribution characteristic $\gamma(\alpha)$ of the illumination optical systems $2a$ and $2b$ obtained from the characteristic of the light guide fiber is indicated below.

TABLE 2

| ANGLE α | 2a ILLUMINANCE γ (α) | 2b ILLUMINANCE γ (α) |
|---|---|---|
| 0 | 1.00 | 1.00 |
| 5 | 0.99 | 0.98 |
| 10 | 0.95 | 0.94 |
| 15 | 0.88 | 0.87 |
| 20 | 0.80 | 0.77 |
| 25 | 0.70 | 0.67 |
| 30 | 0.61 | 0.56 |
| 35 | 0.50 | 0.45 |
| 40 | 0.38 | 0.35 |
| 45 | 0.27 | 0.25 |
| 50 | 0.18 | 0.17 |
| 55 | 0.10 | 0.10 |
| 60 | 0.05 | 0.05 |
| 65 | 0.02 | 0.02 |
| 70 | 0.01 | 0.01 |
| 75 | 0.00 | 0.00 |

Example 2

Figure 9:
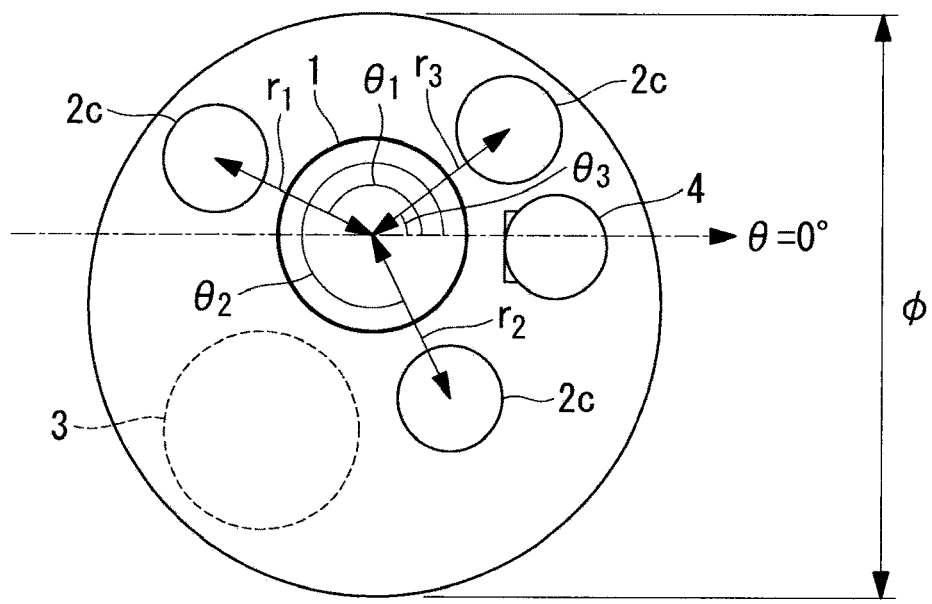
FIG. 9 is a schematic configuration diagram illustrating a front face of a distal end of an insertion portion of an endoscope according to Example 2 of the present invention.
Figure 10:
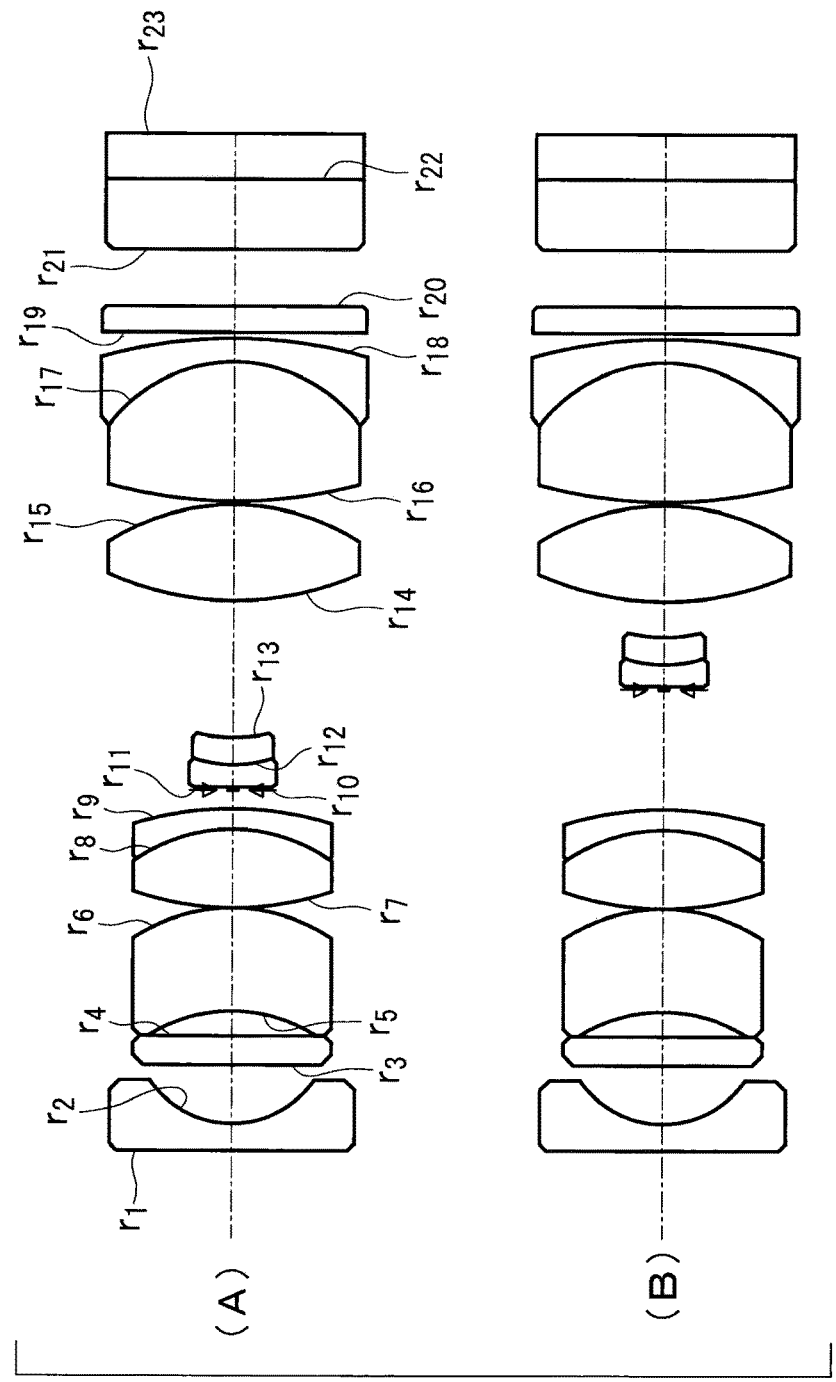
FIG. 10 includes cross-sectional diagrams each illustrating an overall configuration of an observation optical system employed in the endoscope according to Example 2 of the present invention.

A front view of a distal end of an insertion portion of an endoscope according to Example 2 of the present invention is illustrated in FIG. 9. Also, FIG. 10 illustrates a lens configuration of an observation optical system 1 employed in the endoscope according to the present example.

In the present example, $r_1 = 3.99$, $r_2 = 3.84$, $r_3 = 3.80$, $\theta_1 = 28.2°$, $\theta_2 = 157.9°$, $\theta_3 = 294.6°$ and $\phi = 13.2$.

Lens data of the observation optical system according to Example 2 of the present invention are indicated below.

Lensdata

| Surfacenumber | r | d | Nd | Vd |
|---|---|---|---|---|
| Objectsurface | ∞ | d0 | | |
| 1 | ∞ | 0.48 | 1.883 | 40.76 |
| 2 | 21.39 | 0.80 | | |
| 3 | ∞ | 0.40 | 1.521 | 65.13 |
| 4 | ∞ | 0.42 | | |
| 5 | −2.22 | 1.41 | 1.750 | 35.33 |
| 6 | −2.54 | 0.03 | | |
| 7 | 4.56 | 1.07 | 1.773 | 49.6 |
| 8 | −2.42 | 0.37 | 1.923 | 18.9 |
| 9 | −4.67 | 0.29 | | |
| 10(Diaphragm) | ∞ | d10 | | |
| 11 | ∞ | 0.40 | 1.488 | 70.23 |
| 12 | 1.63 | 0.40 | 1.593 | 35.31 |
| 13 | 2.10 | d13 | | |
| 14 | 4.51 | 1.33 | 1.488 | 70.23 |
| 15 | −3.30 | 0.05 | | |
| 16 | 6.34 | 1.92 | 1.488 | 70.23 |
| 17 | −2.19 | 0.48 | 1.923 | 18.9 |
| 18 | −6.59 | 0.03 | | |
| 19 | ∞ | 0.40 | 1.523 | 58.5 |
| 20 | ∞ | 0.63 | | |
| 21 | ∞ | 0.90 | 1.516 | 64.14 |
| 22 | ∞ | 0.60 | 1.505 | 63.26 |
| 23(Imageplane) | ∞ | | | |

Variousdata

| | Normalobservation | Maximummagnification |
|---|---|---|
| d0 | 50 | 2.2 |
| d10 | 0.29 | 1.7 |
| d13 | 1.87 | 0.46 |
| Focallength | 1.49 | 1.72 |
| Front-sidefocalposition | 1.14 | 0.95 |
| Maximumimageheight | 1.6 | 1.6 |
| Paraxialmagnifyingpower | — | −0.55 |
| Pixelpitch | 0.0034 | 0.0034 |

Since the lens configuration of the illumination optical systems is the same as that employed in Example 1, and thus illustration of the lens configuration is omitted, and the lens data are indicated alone. Here, $\phi_L=1.7$, and a clad of a glass rod 16 was formed by glass having a refractive index of 1.520. In this case, $f_L=0.63$ and $f_{L1}=1.13$.

Lensdata

| Surfacenumber | r | d | Nd |
|---|---|---|---|
| 1 | ∞ | 1.35 | 1.883 |
| 2 | −1.01 | 0.06 | |
| 3 | 2.58 | 0.59 | 1.883 |
| 4 | −2.58 | 0.06 | |
| 5 | 1.90 | 2.90 | 1.730 |
| 6 | ∞ | | |

A light guide fiber that is the same as the light guide fiber employed in Example 1 described above was employed, and a light distribution characteristic $\gamma(\alpha)$ of illumination optical system 2c obtained by the characteristic of the light guide fiber is indicated below.

TABLE 3

| | 2c |
|---|---|
| ANGLE α | ILLUMINANCE γ (α) |
| 0 | 1.00 |
| 5 | 0.98 |
| 10 | 0.95 |
| 15 | 0.89 |
| 20 | 0.82 |
| 25 | 0.73 |
| 30 | 0.63 |
| 35 | 0.53 |
| 40 | 0.42 |
| 45 | 0.32 |
| 50 | 0.22 |
| 55 | 0.14 |
| 60 | 0.08 |
| 65 | 0.04 |
| 70 | 0.02 |
| 75 | 0.00 |

Example 3

Figure 11:
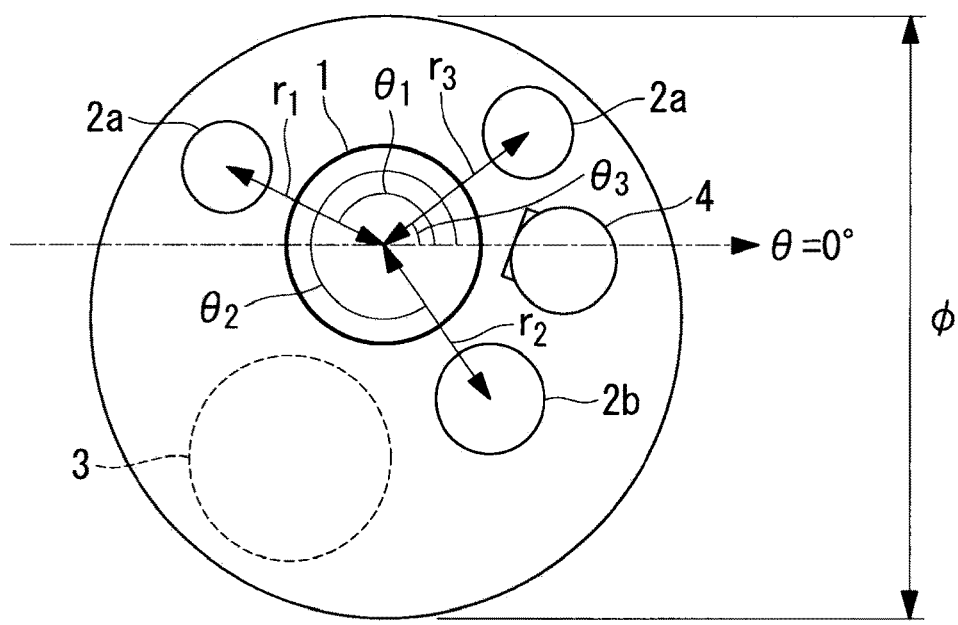
FIG. 11 is a schematic configuration diagram illustrating a front face of a distal end of an insertion portion of an endoscope according to Example 3 of the present invention.
Figure 12:
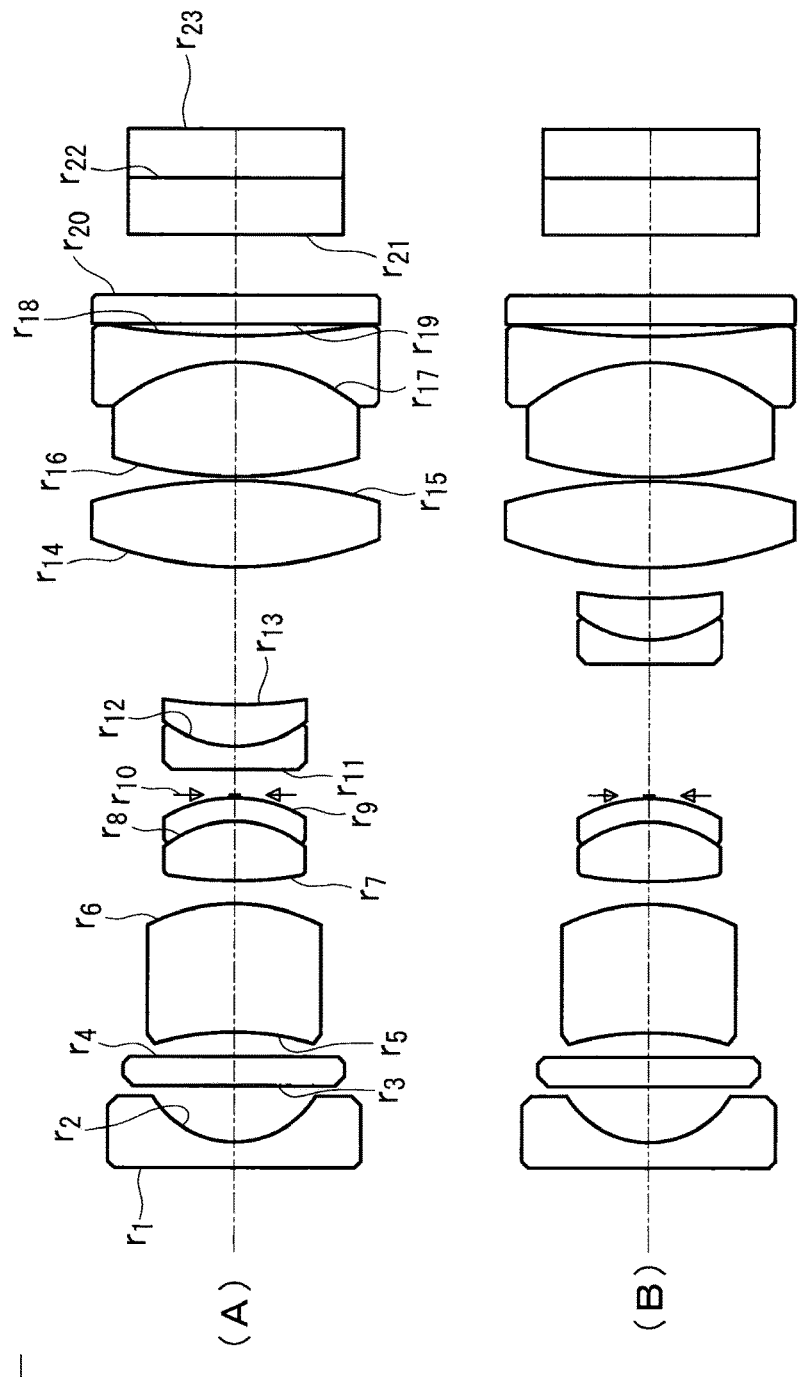
FIG. 12 includes cross-sectional diagrams each illustrating an overall configuration of an observation optical system employed in the endoscope according to Example 3 of the present invention.

A front view of a distal end of an insertion portion of an endoscope according to Example 3 of the present invention is illustrated in FIG. 11. Also, FIG. 12 illustrates a lens configuration of an observation optical system 1 employed in the endoscope according to the present example.

In the present example, $r_1=3.47$, $r_2=3.68$, $r_3=3.47$, $\theta_1=28.4°$, $\theta_2=155.3°$, $\theta_3=303.9°$ and $T=11.7$.

Lens data of an observation optical system according to Example 3 of the present invention are indicated below.

Lensdata

| Surfacenumber | r | d | Nd | Vd |
|---|---|---|---|---|
| Objectsurface | ∞ | d0 | | |
| 1 | ∞ | 0.36 | 1.883 | 40.76 |
| 2 | 1.19 | 0.75 | | |
| 3 | ∞ | 0.40 | 1.521 | 65.13 |
| 4 | ∞ | 0.37 | | |
| 5 | −3.55 | 1.78 | 1.581 | 40.75 |
| 6 | −2.38 | 0.30 | | |
| 7 | 6.83 | 0.83 | 1.517 | 52.43 |
| 8 | −1.38 | 0.30 | 1.923 | 18.9 |
| 9 | −2.14 | 0.05 | | |
| 10(Diaphragm)∞ | | d10 | | |
| 11 | ∞ | 0.31 | 1.773 | 49.6 |
| 12 | 1.42 | 0.58 | 1.728 | 29.46 |
| 13 | 3.67 | d13 | | |
| 14 | 4.68 | 1.20 | 1.816 | 46.62 |
| 15 | −6.02 | 0.03 | | |
| 16 | 4.91 | 1.60 | 1.618 | 63.33 |
| 17 | −2.42 | 0.36 | 1.923 | 18.9 |
| 18 | 11.2 | 0.16 | | |
| 19 | ∞ | 0.40 | 1.523 | 58.5 |
| 20 | ∞ | 0.83 | | |
| 21 | ∞ | 0.80 | 1.516 | 64.14 |
| 22 | ∞ | 0.70 | 1.505 | 63.26 |
| 23(Imageplane) | ∞ | | | |

Variousdata

| | Normalobservation | Maximummagnification |
|---|---|---|
| d0 | 50 | 2.5 |
| d10 | 0.32 | 1.78 |
| d13 | 1.9 | 0.44 |
| Focallength | 1.19 | 1.46 |
| Front-sidefocalposition | 0.99 | 0.78 |
| Maximumimageheight | 1.2 | 1.2 |

-continued

| Normal observation | Maximum magnification |
|---|---|
| Paraxial magnifying power — | −0.45 |
| Pixel pitch 0.0028 | 0.0028 |

A lens configuration and lens data of illumination optical systems are the same as those employed in Example 1 described above, and thus description thereof will be omitted.

Tables 4 and 5 indicate numeral values of conditional expressions (1) to (14) in the configurations of Examples 1 to 3 described above.

TABLE 4

| NUMBER | EXPRESSION | EXAMPLE 1 | EXAMPLE 2 | EXAMPLE 3 |
|---|---|---|---|---|
| (1) | $I_{TC}/I_{TM}$ | 0.42 | 0.30 | 0.35 |
| (2) | $I_{WS}/I_{WC}$ | 0.24 | 0.20 | 0.21 |
| (4) | $r_1{}^2/f_L f_T$ | 13.6 | 14.7 | 15.3 |
| (5) | $r_2{}^2/f_L f_T$ | 13.6 | 13.6 | 12.8 |
| (6) | $f_T F_{FT}/f_W F_{FW}$ | 0.99 | 0.96 | 0.97 |
| (7) | $|1 \times \beta/1_H|$ | 0.41 | 0.34 | 0.37 |
| (8) | $1_H/(1000\, P)$ | 0.29 | 0.47 | 0.43 |
| (11) | $r_1/r_2$ | 1.00 | 1.04 | 0.94 |
| (12) | $|\theta_1 - \theta_2|$ | 180 | 130 | 127 |
| (13) | $r_1 r_2/\phi^2$ | 0.10 | 0.09 | 0.09 |
| (14) | $\min(r_1, r_2, r_3)/\max(r_1, r_2, r_3)$ | — | 0.95 | — |

TABLE 5

| NUMBER | EXPRESSION | EXAMPLE 1 | | EXAMPLE 2 | EXAMPLE 3 | |
|---|---|---|---|---|---|---|
| | | 2a | 2b | 2c | 2a | 2b |
| (3) | $f_L f_T/\phi_L 1_H$ | 0.48 | 0.50 | 0.40 | 0.50 | 0.52 |
| (9) | $f_{L1}/f_L$ | 2.11 | 3.11 | 1.80 | 2.11 | 3.11 |
| (10) | $\gamma(50)/\gamma(25)$ | 0.25 | 0.25 | 0.31 | 0.25 | 0.25 |

According to this aspect, upon conditional expression (1) being satisfied, a ratio of a brightness of a center part relative to a peripheral part can be made high also in a magnified close observation, enabling favorable observation. In other words, in a magnified close observation state, a distance between the observation optical system and a subject is smaller than a distance between the observation optical system and each illumination optical system, and thus, the brightness of the peripheral part is larger than that of the center part. In particular, in a magnified close observation, a lesion or the like to be focused on is usually brought to the center part, and thus, favorable observation cannot be performed unless the ratio of the brightness of the center part relative to that of the peripheral part is high. Thus, satisfaction of conditional expression (1) can make the ratio of the brightness of the center part relative to that of the peripheral part high also in magnified close observation, allowing favorable observation.

In a normal observation state, there is a sufficient distance to a subject, and thus, a brightness of a center part is larger than that of a peripheral part. Also, in this state, a subject having a depth is observed, and an excessive increase in brightness of the peripheral part may hinder favorable observation in the depth direction. On the other hand, an excessive decrease in brightness of the peripheral part may hinder favorable observation of the peripheral part, and thus it is necessary to balance the brightness for observation in the depth direction and the brightness for observation of the peripheral part. Thus, the endoscope is configured so as to satisfy conditional expression (2).

In order to satisfy both conditional expressions (1) and (2), it is necessary to set the focal length of each illumination optical system so as to conform to a focal length of the observation optical system, and also to satisfy conditional expression (3). As a result of conditional expression (3) being satisfied, the focal length of the observation optical system and the focal length of each illumination optical system are determined, enabling provision of a well-balanced light distribution capability for both of distant observation and close observation.

Also, in the above aspect, it is preferable that at least two illumination optical systems of the plurality of illumination optical systems satisfy the following conditional expressions:

$$8 < r_1{}^2/f_L f_T < 16 \qquad (4); \text{ and}$$

$$8 < r_2{}^2/f_L f_T < 16 \qquad (5),$$

where each of $r_1$ and $r_2$ is a distance between a center of a lens disposed farthest on an object side of the observation optical system, and a center of the lens disposed farthest on the object side of each of the illumination optical systems.

Consequently, the distance between the observation optical system and each illumination optical system falls within a desired range, enabling setting of a proper light distribution capability of the illumination optical system.

Also, in the above aspect, it is preferable that the observation optical system satisfies the following conditional expression:

$$0.8 < f_T F_{FT}/f_W F_{FW} < 1.1 \qquad (6),$$

where $f_W$ is a focal length of the entire system in a normal observation state, $F_{FT}$ is a front-side focal position in a magnified close observation state, and $F_{FW}$ is a front-side focal position in a normal observation state.

Consequently, the view field range can be made to fall within a proper range, enabling provision of even light distribution and thus favorable observation.

Also, in the above aspect, it is preferable that the observation optical system satisfies the following conditional expression:

$$0.3 < |1 \times \beta/I_H| < 0.45 \qquad (7),$$

where $\beta$ is a paraxial magnifying power of the observation optical system in a maximum magnification.

Consequently, a sufficient magnification factor can be provided in a maximum magnification, enabling favorable observation of a subject.

Also, in the above aspect, it is preferable that the observation optical system satisfies the following conditional expression:

$$0.25 < I_H/(1000P) < 0.5 \qquad (8),$$

where P is a pixel pitch of an image pickup device included in the observation optical system.

Consequently, an image pickup device including a sufficient number of pixels can be employed, enabling favorable observation.

Also, in the above aspect, it is preferable that at least two illumination optical systems of the plurality of illumination optical systems each include three convex lenses and satisfy the following conditional expression:

$$1.4 < f_{L1}/f_L < 3.2 \qquad (9),$$

where $f_{L1}$ is a focal length of a lens that is farthest on an object side of each illumination optical system.

Consequently, a proper light distribution range is provided, enabling favorable observation.

Also, in the above aspect, it is preferable that in at least two illumination optical systems of the plurality of illumination optical systems, where a brightness in a direction toward a center at a distance of 50 mm is 1, a brightness $\gamma(\alpha)$ at an arbitrary angle $\alpha$ (°) satisfies the following conditional expression:

$$0.21 < \gamma(50)/\gamma(25) < 0.39 \qquad (10).$$

Consequently, an amount of variation in an angular direction in a light distribution capability of each illumination optical system is suppressed, enabling maintenance of a proper light distribution capability.

Also, in the above aspect, it is preferable that at least two illumination optical systems of the plurality of illumination optical systems satisfy the following conditional expressions:

$$0.8 < r_1/r_2 < 1.2 \qquad (11);$$

$$165 < |\theta_1 - \theta_2| \le 180 \qquad (12); \text{ and}$$

$$0.06 < r_1 r_2/\phi^2 < 0.15 \qquad (13),$$

where each of $\theta_1$ and $\theta_2$ is an azimuth relative to the direction toward the center, and $\phi$ is a diameter of a distal end of the endoscope.

Consequently, proper arrangement of the observation optical system and the illumination optical systems can be made, enabling suppression of concentration of illuminating light on a subject or light distribution unevenness.

Also, in the above aspect, it is preferable that three of the illumination optical systems are provided, and the illumination optical systems are illumination optical systems that are identical to one another and each include three convex lenses, and satisfy the following conditional expressions:

$$0.8 < \min(r_1, r_2, r_3)/\text{Max}(r_1, r_2, r_3) \le 1.0 \qquad (14),$$

where each of $r_1$, $r_2$ and $r_3$ is a distance between a center of a lens disposed farthest on an object side of the observation optical system, and a center of the lens disposed farthest on the object side of the relevant illumination optical system.

Consequently, proper arrangement of the three illumination optical systems can be made, enabling suppression of concentration of illuminating light on a subject or light distribution unevenness.

In other words, not only the observation optical system and the illumination optical systems, but also structural objects such as a channel for letting a treatment instrument out and a nozzle for cleaning lenses are arranged. Thus, in particular, where three illumination optical systems are arranged, it may be difficult to arrange all the illumination optical systems symmetrically with reference to an observation optical system. In this case, it is preferable that respective distances of the three illumination optical systems from the observation optical system be made to be equal to one another, and it is preferable that conditional expression (14) be satisfied.

Advantageous Effects of Invention

The present invention provides the effect of ensuring sufficient light distribution and thereby allowing favorable observation in both normal observation and close observation.

REFERENCE SIGNS LIST 1 observation optical system
2 illumination optical system
3 channel
4 nozzle

The invention claimed is:

1. An endoscope comprising:
an observation optical system provided in a distal end of an insertion portion, the observation optical system including a plurality of lenses and having a function that allows a magnified observation close to a subject; and
a plurality of illumination optical systems provided in the distal end of the insertion portion, the plurality of illumination optical systems each including a plurality of lenses and illuminating the subject with illuminating light,
wherein the plurality of illumination optical systems include a first illumination optical system and a second illumination optical system different from the first illumination optical system,
each of the first and second illumination optical systems satisfies the following conditional expression (3),
in a close observation in which a distance between a distal end face of the insertion portion and the subject is an arbitrary distance of from 1.5 mm to 2.5 mm, where $I_{TM}$ is a maximum brightness within an observation view field angle and $I_{TC}$ is a center brightness, and
in a normal observation in which the distance between the distal end face of the insertion portion and the subject is 50 mm, where $I_{WC}$ is a center brightness and $I_{WS}$ is a brightness at a position of 80% of a maximum view angle, the following conditional expressions are satisfied:

$$0.3 < I_{TC}/I_{TM} < 0.45 \qquad (1);$$

$$0.15 < I_{WS}/I_{WC} < 0.25 \qquad (2); \text{ and}$$

$$0.3 < f_L f_T/\phi_L I_H < 0.6 \qquad (3),$$

where $f_L$ is a focal length of each of the entire illumination optical systems, $f_T$ is a focal length of the entire observation optical system in a maximum magnification, $\phi_L$ is an outer diameter of a lens that is farthest on an object side of each illumination optical system, and $I_H$ is a maximum image height of the observation optical system.

2. The endoscope according to claim 1, wherein each of the first and second illumination optical systems satisfies the following conditional expression:

$$8 < r^2/f_L f_T < 16 \qquad (4'),$$

where r is a distance between a center of a lens disposed farthest on an object side of the observation optical system, and a center of the lens disposed farthest on the object side of each of the illumination optical systems.

3. The endoscope according to claim 1, wherein the observation optical system satisfies the following conditional expression:

$$0.8 < f_T F_{FT}/f_W F_{FW} < 1.1 \qquad (6),$$

where $f_W$ is a focal length of the entire system in a normal observation state, $F_{FT}$ is a front-side focal position in a magnified close observation state, and $F_{FW}$ is a front-side focal position in a normal observation state.

4. The endoscope according to claim 3, wherein the observation optical system satisfies the following conditional expression:

$$0.3<|1\times\beta/I_H|<0.45 \quad (7),$$

where $\beta$ is a paraxial magnifying power of the observation optical system in a maximum magnification.

5. The endoscope according to claim 3, wherein the observation optical system satisfies the following conditional expression:

$$0.25<I_H/(1000P)<0.5 \quad (8),$$

where P is a pixel pitch of an image pickup device included in the observation optical system.

6. The endoscope according to claim 2, wherein the first and second illumination optical systems each include three convex lenses and satisfy the following conditional expression:

$$1.4<f_{L1}/f_L<3.2 \quad (9),$$

where $f_{L1}$ is a focal length of a lens that is farthest on an object side of each illumination optical system.

7. The endoscope according to claim 2, wherein in at least two illumination optical systems of the plurality of illumination optical systems, where a brightness in a direction toward a center at a distance of 50 mm is 1, a brightness $\gamma$ ($\alpha$) at an arbitrary angle $\alpha$ (°) satisfies the following conditional expression:

$$0.21<\gamma(50)/\gamma(25)<0.39 \quad (10).$$

8. The endoscope according to claim 2, wherein at least two illumination optical systems of the plurality of illumination optical systems satisfy the following conditional expressions:

$$0.8<r_1/r_2<1.2 \quad (11);$$

$$165<|\theta_1-\theta_2|\leq180 \quad (12); \text{ and}$$

$$0.06<r_1r_2/\phi^2<0.15 \quad (13),$$

where each of $\theta_1$ and $\theta_2$ is an azimuth relative to the direction toward the center, and $\phi$ is a diameter of the distal end of the endoscope.

9. The endoscope according to claim 1, wherein three of the illumination optical systems are provided, and the illumination optical systems are illumination optical systems that are identical to one another and each include three convex lenses, and satisfy the following conditional expression:

$$0.8<\min(r_1,r_2,r_3)/\text{Max}(r_1,r_2,r_3)\leq1.0 \quad (14),$$

where each of $r_1$, $r_2$ and $r_3$ is a distance between a center of a lens disposed farthest on an object side of the observation optical system, and a center of the lens disposed farthest on the object side of the relevant illumination optical system.

* * * * *